(12) United States Patent
Plessala et al.

(10) Patent No.: US 11,020,146 B2
(45) Date of Patent: Jun. 1, 2021

(54) DEVICE AND METHOD FOR ARTIFICIAL INSEMINATION

(71) Applicant: InnoMed One, LLC, Mobile, AL (US)

(72) Inventors: Kirby J. Plessala, Mobile, AL (US); Peter T Falkner, Mobile, AL (US)

(73) Assignee: InnoMed One, LLC, Mobile, AL (US)

( * ) Notice: Subject to any disclaimer, the term of this patent is extended or adjusted under 35 U.S.C. 154(b) by 123 days.

(21) Appl. No.: 16/349,159

(22) PCT Filed: Nov. 30, 2017

(86) PCT No.: PCT/US2017/064028
§ 371 (c)(1),
(2) Date: May 10, 2019

(87) PCT Pub. No.: WO2018/102590
PCT Pub. Date: Jun. 7, 2018

(65) Prior Publication Data
US 2019/0282271 A1    Sep. 19, 2019

Related U.S. Application Data

(63) Continuation of application No. PCT/US2016/064243, filed on Nov. 30, 2016.

(51) Int. Cl.
*A61B 17/43* (2006.01)
*A61M 25/01* (2006.01)
(Continued)

(52) U.S. Cl.
CPC ............. *A61B 17/43* (2013.01); *A61M 25/01* (2013.01); *A61B 17/12159* (2013.01); *A61B 2017/4225* (2013.01); *A61M 31/00* (2013.01)

(58) Field of Classification Search
CPC ................ A61B 17/43; A61B 17/4241; A61B 2017/4225; A61M 31/00
See application file for complete search history.

(56) References Cited

U.S. PATENT DOCUMENTS 5,928,249 A    7/1999  Saadat

FOREIGN PATENT DOCUMENTS

| CN | 201029975 | 3/2008 |
|----|-----------|--------|
| WO | 97-22309  | 6/1997 |

OTHER PUBLICATIONS

Jang, Giejeong; International Search Report by International Search Authority (European Patent Office) for PCT/US2017/064028.
(Continued)

*Primary Examiner* — Julie A Szpira
(74) *Attorney, Agent, or Firm* — Intellectual Property Consulting, LLC; Stephen M. Kepper

(57) ABSTRACT

A medical device and method for artificial insemination are provided. The medical device has a shield and an arm secured to the shield at one end and extending outwardly from the shield. The arm is inserted into the cervical canal of a patient and the shield covers the external os of the patient. By inserting the medical device into a patient's cervical canal after insemination, a physical barrier that holds a semen sample within the cervical canal and prevents leakage from the cervical canal back into the vaginal cavity is established. The device may have a bore extending through the device for a catheter to pass through. The bore has a valve to allow passage of the catheter and prevent backflow of semen. The arm may have a circumferential bulge to help keep the device in place during use.

9 Claims, 7 Drawing Sheets

(51) Int. Cl.
    *A61B 17/12*     (2006.01)
    *A61M 31/00*     (2006.01)
    *A61B 17/42*     (2006.01)

(56)           References Cited

OTHER PUBLICATIONS

Jang, Giejeong; Written Opinion by International Search Authority (European Patent Office) for PCT US2017/064028.

DEVICE AND METHOD FOR ARTIFICIAL INSEMINATION

CROSS REFERENCES

This application claims priority to PCT Application No. PCT/US2016/064243, filed on Nov. 30, 2016, which application is incorporated herein by reference.

FIELD OF THE INVENTION

A preferred implementation of the present invention refers generally to a device and method for artificial insemination.

BACKGROUND

Artificial insemination aims to introduce sperm into the reproductive system of a patient to promote pregnancy. Typically, artificial insemination is carried out when it is difficult or impossible for sperm to enter a patient's reproductive system during sexual intercourse. Intracervical insemination, where a semen sample is introduced into a patient's cervical canal, and intrauterine insemination, where a semen sample is introduced into a patient's uterine cavity, are two common artificial insemination procedures currently used. Generally, during such procedures, a patient's vaginal walls are held open by a medical device, such as a speculum. A semen sample is then introduced into to the patient's cervical canal or uterine cavity, depending on which procedure is being performed, typically via a catheter-syringe assembly. After introduction of the semen sample, the semen is left to take by the patient's reproductive system. However, a portion of the semen sample may be lost by leaking from the cervical canal into the vaginal cavity of the patient due to reflux caused by uterine contractions.

Some known devices, such as vaginal sponges and cervical caps, attempt to solve the problem of leaking by creating a barrier between the patient's cervical canal and vaginal cavity after the semen sample is introduced. However, these devices merely attempt to blockade the upper region of the patient's vaginal cavity near the patient's cervical canal and may not effectively hold the semen sample within the cervical canal. Thus, the use of vaginal sponges and cervical caps in artificial insemination may not be effective in preventing a reduction in the efficacy of the insemination procedure due to reflux caused by uterine contractions. These devices may also cause patient discomfort when inserted and removed.

The device disclosed in application PCT/US2016/064243, filed by the present Applicant, attempts to solve the above-outlined problems. This device is designed to be inserted into the cervical canal and remain in place for a period of time during which insemination occurs while preventing leakage of semen from the cervical canal. The device may also allow a catheter to be inserted through a bore extending through the device so that semen may be introduced into the cervical canal or uterine cavity while the device is in place in a patient's cervical canal. However, the device may sometimes become dislodged from the cervical canal during the period of time in which the device is intended to remain in place to allow insemination to occur, or a small amount of leakage may occur through the bore that extends through the device.

Accordingly, a need exists in the art for a device for increasing the efficacy of artificial insemination procedures and for a method of using the device. Furthermore, a need exists in the art for a device for increasing the efficacy of artificial insemination procedures without causing significant patient discomfort upon insertion and removal of the device.

SUMMARY

The present disclosure provides a device and methods for artificial insemination in accordance with the independent claims. Preferred embodiments of the invention are reflected in the dependent claims. The claimed invention can be better understood in view of the embodiments described and illustrated in the present disclosure, viz. in the present specification and drawings. In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the invention per se.

In one aspect of the present disclosure, a medical device for use during artificial insemination in order to prevent semen sample leakage from the cervical canal of a patient is provided. The medical device may be configured to function as a cervical plug. The medical device has a shield configured to cover an orifice and an arm having a proximal end and a distal end. The proximal end is secured to the shield, and the distal end is configured to insert into the orifice. For instance, the shield may be configured to cover the orifice between a patient's cervical canal and vaginal cavity ("external os"), and the arm may be configured to insert into the patient's cervical canal. Due to the arm's insertion within the cervical canal and the shield's coverage of the external os, the medical device may effectively secure itself in place during use. The arm may have a circumferential bulge positioned near the distal end of the arm to help keep the device in place with the arm inserted into the cervical canal during use.

By inserting the medical device through the vaginal cavity and into the cervical canal of a patient such that the arm is inserted into the patient's cervical canal and the shield covers the patient's external os, the medical device may establish a physical barrier that holds a semen sample within the patient's cervical canal and prevents leakage into the vaginal cavity. In this manner, the medical device may be utilized as a cervical plug after a semen sample is introduced into the cervical canal or uterine cavity of a patient to prevent the semen sample from leaking into the vaginal cavity, thereby preventing semen sample loss. Accordingly, the present disclosure may also be directed toward a method for artificial insemination wherein a semen sample is first introduced into a patient's cervical canal or uterine cavity, and the medical device is then inserted into the patient's cervical canal in the manner described above.

In addition, the medical device may be configured to function as both a cervical plug as well as a guide or cannula for a catheter. The medical device has a shield and an arm having a proximal end and a distal end. The proximal end is secured to the shield, and the distal end is configured to insert into the patient's cervical canal. The medical device may further have a bore extending longitudinally through the arm and through the shield such that the bore has an opening at the distal end of the arm and an opening on the side of the shield opposite the arm. A valve that is operable between an open position and a closed position may be disposed at the distal end of the arm. The valve comprises a plurality of elastomeric flaps integrally attached to the distal end of the arm. The elastomeric flaps are resiliently biased inwardly toward the center of the bore and against each other when the valve is in the closed position. The elastomeric flaps are sized and shaped to form a substantially fluid-tight seal over the opening at the distal end of the arm when the valve is in the closed position. To use the device, a catheter may be inserted into the opening of the bore on the side of the shield opposite the arm and pushed through the opening at the distal end of the arm. When pushed through the opening at the distal end of the arm, the catheter forces the elastomeric flaps of the valve outward, thereby moving the valve into the open position. In this manner, a catheter may pass through the medical device, deliver a semen sample to a patient's cervical canal or uterine cavity, and then be removed from the medical device while leaving the device in place. When the catheter is removed, the valve moves to the closed position such that the semen sample cannot leak back through the medical device into the vaginal cavity. Accordingly, the present disclosure may also be directed toward a method for artificial insemination wherein the medical device is inserted into a patient's cervical canal in the manner described above, a catheter is inserted into the bore of the medical device, a semen sample is directed through the catheter into the patient's cervical canal or uterine cavity, and the catheter is then removed leaving the medical device in place.

To insert and remove the medical device, the medical device may have an insert member secured to the shield on the opposite side of the shield as the arm. The insert member may have a string secured thereto in order to facilitate removal of the medical device. To minimize patient discomfort during insertion and removal of the medical device, the shield may be made of a flexible material.

Additional features and advantages of the present disclosure will be set forth in the description which follows, and will be apparent from the description, or may be learned by practice of the present disclosure. The foregoing general description and following detailed description are exemplary and explanatory and are intended to provide further explanation of the present disclosure.

DESCRIPTION OF THE DRAWINGS

These and other features, aspects, and advantages of the present disclosure will become better understood with regard to the following description, appended claims, and accompanying drawings where:

DETAILED DESCRIPTION

Figure 1:
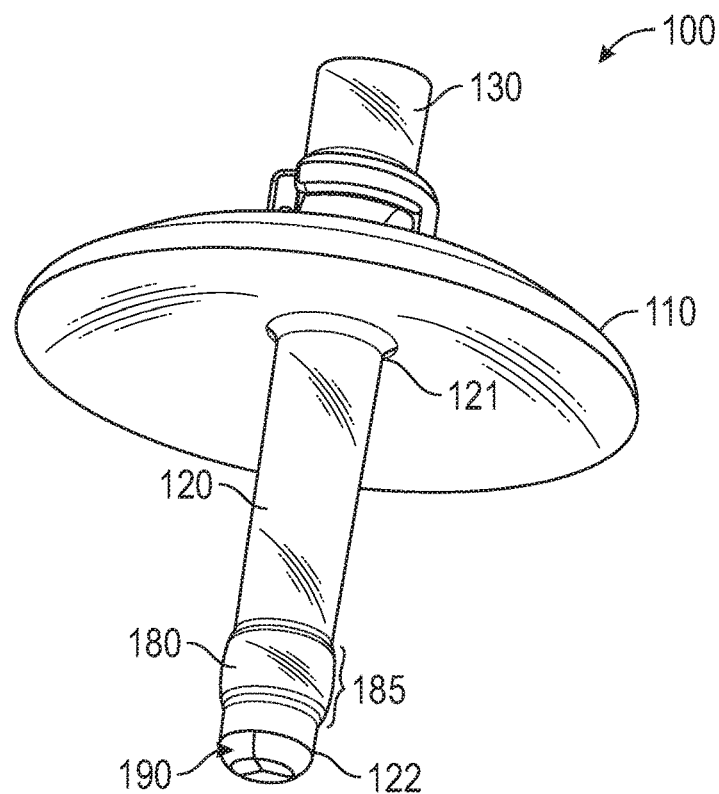
FIG. 1 shows a perspective view of a device in accordance with the present disclosure.

In the Summary above and in this Detailed Description, and the claims below, and in the accompanying drawings, reference is made to particular features, including method steps, of the invention as claimed. In the present disclosure, many features are described as being optional, e.g. through the use of the verb "may" or the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features, or with all three of the three possible features. It is to be understood that the disclosure in this specification includes all possible combinations of such particular features. For example, where a particular feature is disclosed in the context of a particular aspect or embodiment, or a particular claim, that feature can also be used, to the extent possible, in combination with/or in the context of other particular aspects or embodiments, and generally in the invention as claimed.

The term "comprises" and grammatical equivalents thereof are used herein to mean that other components, ingredients, steps, etc. are optionally present. For example, an article "comprising" components A, B, and C can contain only components A, B, and C, or can contain not only components A, B, and C, but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Turning now to the drawings, FIGS. 1-14 illustrate embodiments of a medical device for holding materials in and preventing material leakage from an orifice. The medical device 100 may be designed to function as a cervical plug for holding semen in and preventing semen leakage from the cervical canal 730 of a patient after a semen sample is introduced into the patient's cervical canal 730 or uterine cavity 740. The medical device 100 has a shield 110 configured to cover an orifice and an arm 120 configured to insert into the orifice, wherein one end of the arm 120 is secured to the shield 110. The shield 110 may be configured to cover a patient's external os 720, and the arm 120 may be configured to insert into the patient's cervical canal 730, as illustrated in FIG. 14. By inserting the medical device 100 through the vaginal cavity 710 and into the cervical canal 730 of a patient such that the arm 120 is inserted into the patient's cervical canal 730 and the shield 110 covers the patient's external os 720, the medical device 100 may establish a physical barrier between a patient's cervical canal 730 and vaginal cavity 710. In this manner, the medical device 100 may function as a cervical plug that prevents leakage of a semen sample from the cervical canal 730 into the vaginal cavity 710 after the semen sample has been introduced into the cervical canal 730 or uterine cavity 740 of a patient.

It should be understood that the medical device may be utilized for covering and plugging other bodily orifices including, but not limited to, the internal orifice of the cervix, without departing from the scope of the present disclosure.

As illustrated in FIGS. 1-5, the medical device 100 comprises a shield 110 and an arm 120 secured to the shield 110. To accommodate the contours of the portion of the cervix surrounding a patient's external os 720, the shield 110 may have a concave shape having a concave side and a convex side, wherein the concave side of the shield 110 faces the external os 720 and the convex side faces the vaginal cavity 710 when the medical device 100 is in place, as shown in FIG. 14. The shield 110 may be shaped such that the concave side of the shield 110 fits flush against the external os 720 and cervical tissue surrounding the external os of the patient. The curvature of the shield 110 may be adjusted for different patients. The arm 120 may be secured to the concave side of the shield 110, as shown in FIG. 1. In addition, the shield 110 may have a generally circular shape, and the arm 120 may be secured to the shield 110 generally at the center of the shield, as shown in FIG. 1. Alternatively, the shield may be of another shape suitable for covering the external os 720 of a patient, such as an elliptical shape.

The shield 110 may be shaped and sized such that the shield 110 can cover the external os 720 of nulliparous, primiparous, or multiparous women. To minimize pain or discomfort experienced by a patient as the medical device 100 is inserted or removed from the patient's body, the shield 110 may be made of a material that is somewhat flexible such that the material may be deformed by pressure applied by a user of the device but return to its original shape when the pressure is removed. Alternatively, the shield 110 may be made of a material that is substantially rigid or semi-rigid. In addition, the shield 110 may be made of a material that is at least partially translucent or transparent, which may aid a user in inserting the device in the cervical canal. Alternatively, the shield 110 may be made of an opaque material. The shield 110 may comprise medical-grade silicone rubber. However, the shield may be made of any suitable material including, but not limited to, plastic, glass, ceramic, metal, any type of rubber, or any combination thereof.

The arm 120 of the medical device 100 is configured to insert into the orifice covered by the shield 110 when the medical device 100 is in use. The arm 120 is an elongated member having a proximal end 121 and a distal end 122. The proximal end 121 is secured to the shield 110, and the distal end 122 is inserted into the orifice when the device is in use. The arm 120 may be permanently secured to the shield 110. For instance, the arm 120 and shield 110 may be molded as a unitary piece of material. Alternatively, the arm 120 may be secured to the shield 110 with an adhesive. To facilitate ease of entry and exit of the arm 120 into and out of a patient's cervical canal 730, the arm 120 may have a generally cylindrical shape.

Figure 4:
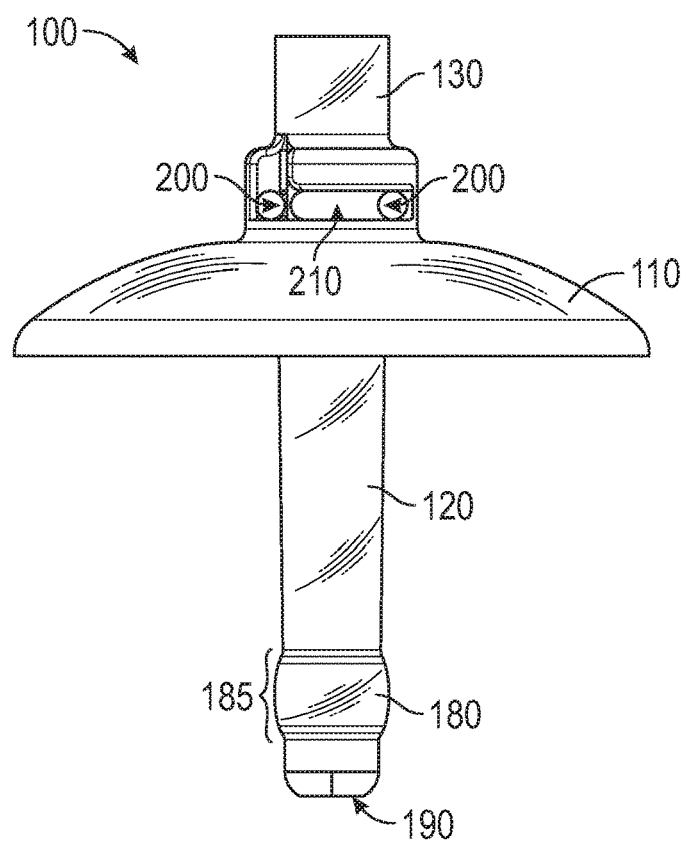
FIG. 4 shows an elevational view of a device in accordance with the present disclosure.

The arm 120 may have a circumferential bulge 180 to help keep the device 100 in place with the arm 120 inserted into the cervical canal 730 during use. The bulge 180 is positioned along a length 185 of the arm 120 between a midway point of the arm (midway between the proximal end 121 and the distal end 122) and the distal end 122 of the arm, and may preferably be positioned nearer to the distal end 122 of the arm 120 than to the midway point of the arm 120, as shown in FIG. 1. Once the arm 120 is inserted into the cervical canal 730, as shown in FIG. 14, the wider diameter of the circumferential bulge 180 provides resistance to removal of the arm 120 from the cervical canal 730, thereby helping to keep the device 100 in place for a period of time after semen has been introduced into the cervical canal 730 or uterine cavity 740 so that the device 100 prevents leakage of semen from the cervical canal 730 into the vaginal cavity 710. As shown in FIG. 4, the bulge 180 preferably has a contoured surface to prevent discomfort when inserting the arm 120 into the cervical canal 730.

The arm 120 is sufficiently rigid for inserting the arm 120 into the cervical canal 730 of a patient, but the arm 120 may have some amount of flexibility in order to minimize pain or discomfort experienced by the patient as the device 100 is inserted or removed. Alternatively, the arm 120 may be made of a material that is substantially rigid. In addition, the arm 120 may be made of a material that is at least partially translucent or transparent. Alternatively, the arm 120 may be made of an opaque material. The arm 120 may comprise medical-grade silicone rubber. However, the arm may be made of any suitable material including, but not limited to, plastic, glass, ceramic, metal, any type of rubber, or any combination thereof.

The shield 110 and the arm 120 may be configured to secure the medical device 100 in place during use, as shown in FIG. 14, such that the shield 110 remains covering an orifice until the medical device 100 is removed by a user. As used herein, the terms "during use" or "in use" refer to any point when the arm 120 of the medical device 100 is inserted into an orifice and the shield 110 of the medical device 100 is covering the orifice. FIG. 14 illustrates the device 100 being used with a syringe 170 and catheter 160 for introducing semen into the reproductive system. However, as discussed below, the syringe 170 and catheter 160 are removed after the introduction of semen, and the device 100 remains in place in the position shown in FIG. 14 for a period of time to prevent leakage of semen into the vaginal cavity 710. The proximal end 121 of the arm 120 may have a diameter of sufficient size such that when the proximal end 121 of the arm 120 is positioned in the cervical canal 730 of a patient after insertion of the device, a substantially fluid-tight seal is formed between the cervical canal 730 and the vaginal cavity 710 of the patient. The fluid-tight seal formed by insertion of the arm 120 into the cervical canal 730 may facilitate a slight suction between the concave shield 110 and the area of the cervix covered by the shield 110, thereby further securing the medical device 100 in place. When secured in place, the shield 110 may substantially cover the external os 720 and fit flush against the tissue surrounding the external os 720 such that the shield 110, in conjunction with the arm 120, may prevent leakage of a sperm sample around the device 100 and into the vaginal cavity 710.

Figure 5:
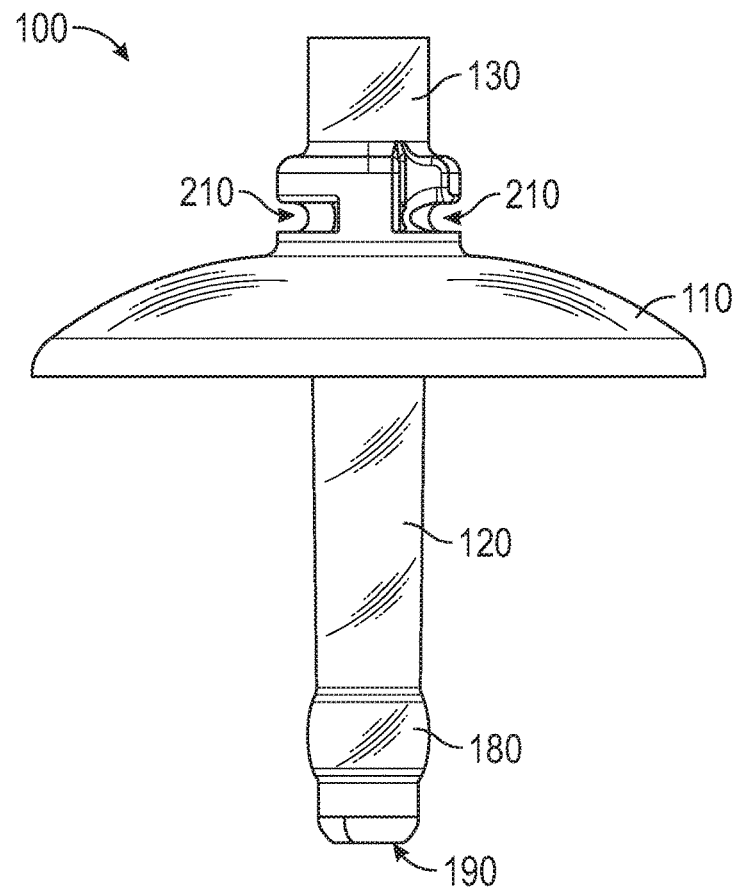
FIG. 5 shows an elevational view of a device in accordance with the present disclosure.

As illustrated in FIGS. 3-6, the medical device 100 may further comprise an insert member 130 secured to the shield 110. The insert member 130 may function as an aid for inserting the medical device 100 into the cervical canal 730 and removing the device from the cervical canal. The insert member 130 is secured to the opposite side of the shield 110 as the proximal end 121 of the arm 120. The insert member 130 may be permanently secured to the shield 110. For instance, the medical device 100 may be molded as a unitary piece of material including the shield 110, arm 120, and insert member 130. Alternatively, the insert member 130 may be secured to the shield 110 with an adhesive. As illustrated in FIGS. 4 and 5, the insert member 130 may be secured to the shield 110 such that the insert member 130 forms a generally straight line with the arm 120.

The insert member 130 provides a protrusion that may be grabbed using forceps for the purpose of guiding the device to insert or remove the medical device 100. The insert member 130 may be sufficiently rigid to retain its shape such that it can be grabbed using forceps or a similar device. Alternatively, the insert member 130 may be somewhat flexible. In addition, the insert member 130 may be made of a material that is at least partially translucent or transparent. Alternatively, the insert member 130 may be made of an opaque material. The insert member 130 may comprise medical-grade silicone rubber. However, the insert member may be made of any suitable material including, but not limited to, plastic, glass, ceramic, metal, any type of rubber, or any combination thereof.

Figure 6:
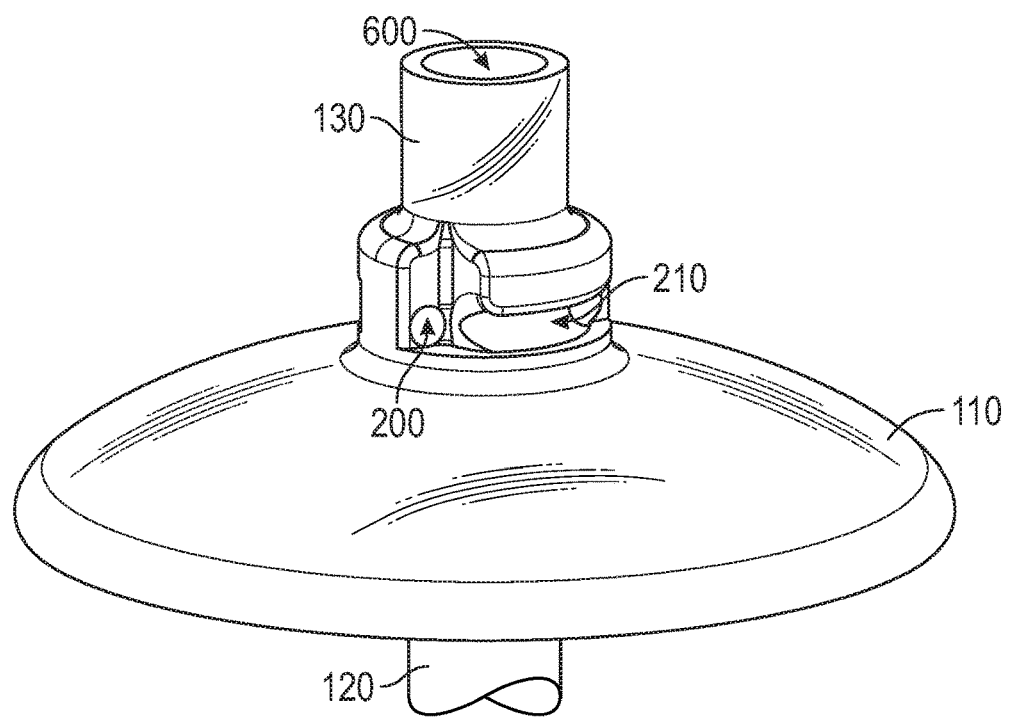
FIG. 6 shows a partial perspective view of a device in accordance with the present disclosure.
Figure 7:
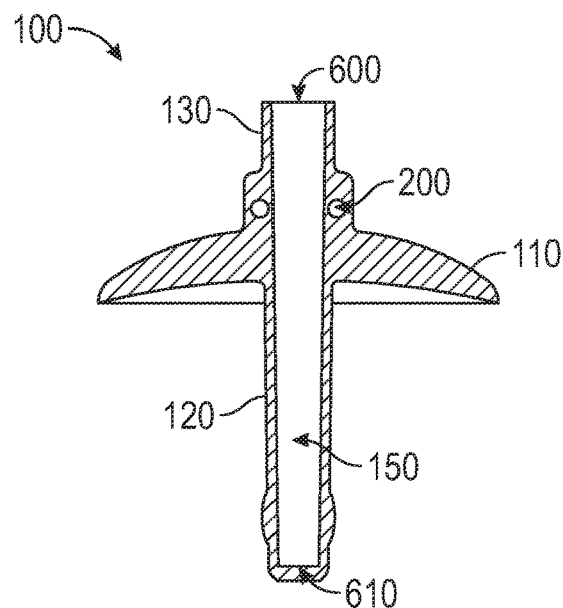
FIG. 7 shows a cross-sectional view of a device in accordance with the present disclosure.
Figure 8:
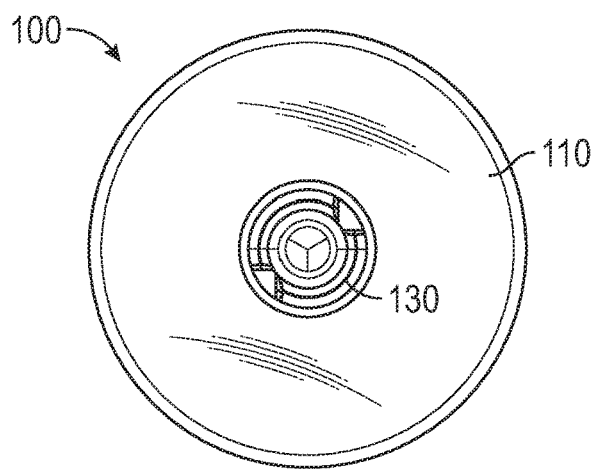
FIG. 8 shows a top plan view of a device in accordance with the present disclosure.
Figure 10:
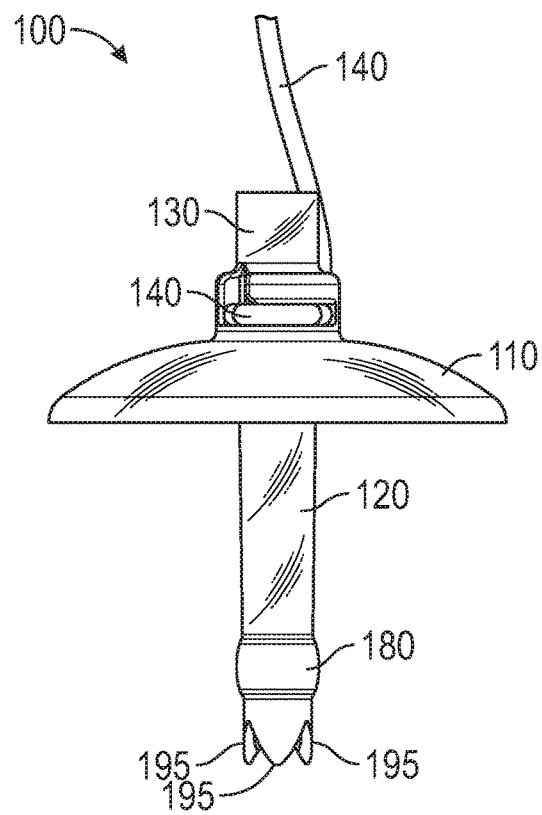
FIG. 10 shows an elevational view of a device in accordance with the present disclosure.
Figure 13:
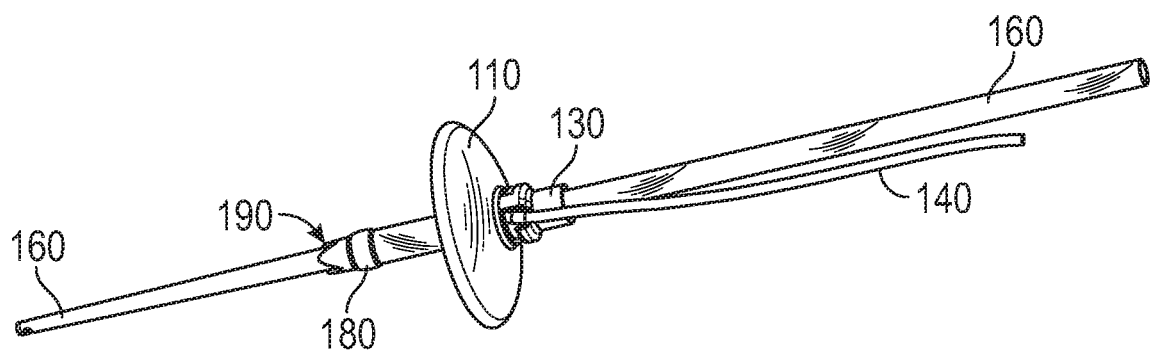
FIG. 13 shows a perspective view of a device with a catheter inserted through the device in accordance with the present disclosure.
Figure 14:
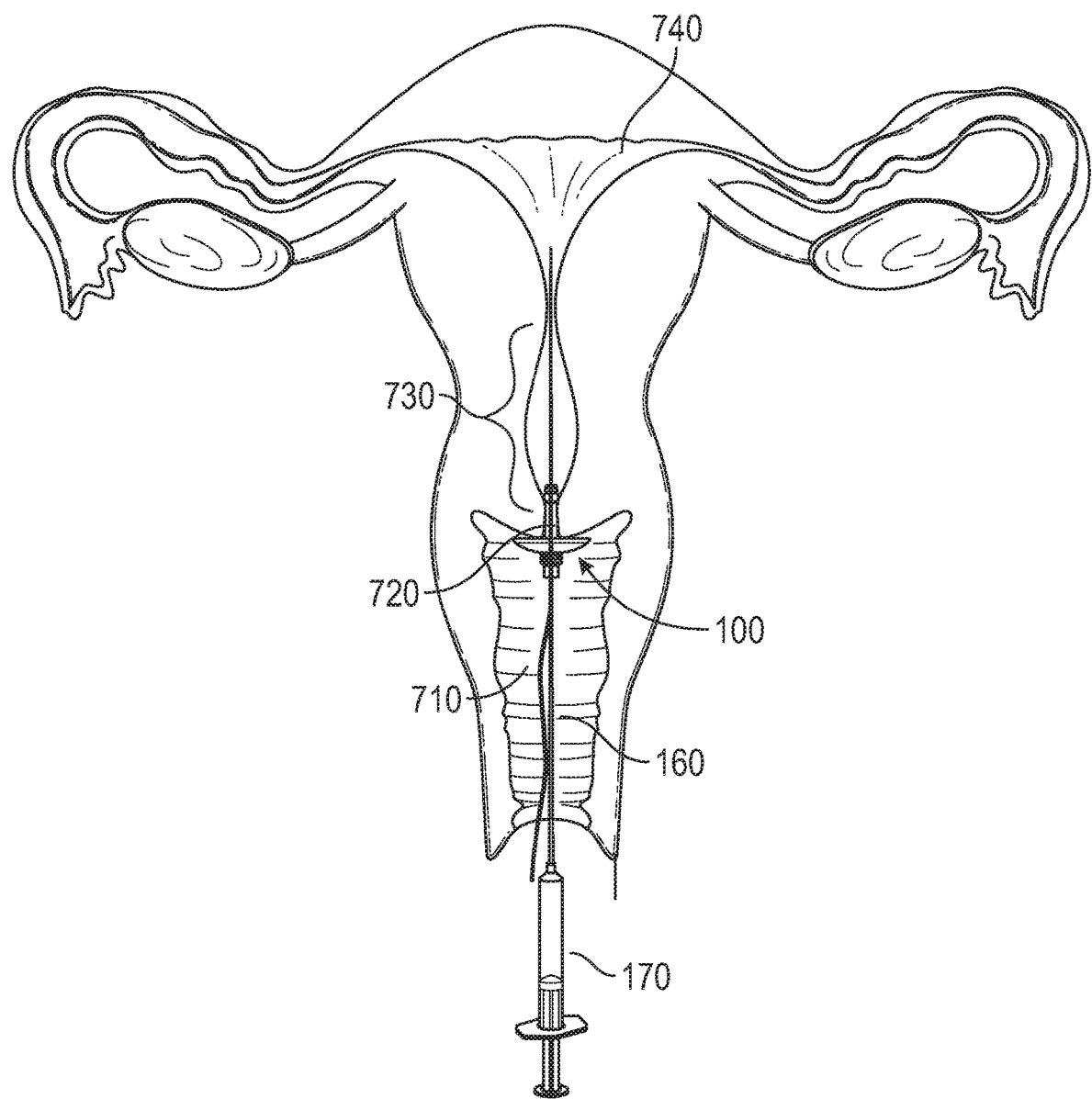
FIG. 14 shows a device in accordance with the present disclosure inserted in a patient's reproductive system, said device being used with a catheter and syringe

To facilitate removal of the medical device 100 after use, the insert member 130 may optionally have a string 140 attached thereto, as best seen in FIGS. 10 and 13. The string 140 may be a medical-grade suture, though any suitable material may be utilized. To facilitate attachment of the string 140 to the insert member 130, the insert member 130 may have an annular cavity 200 located on the exterior of the insert member 130, as best seen in FIGS. 6 and 7. The insert member 130 has at least one external opening 210 that provides external access to the annular cavity 200. Preferably, as best seen in FIG. 5, the insert member 130 has two external openings 210 on opposing sides of the insert member 130. To secure the string 140 to the insert member 130, an end of the string 140 may be inserted through the external opening 210 into the annular cavity 200 and around the insert member 130 until the inserted end of the string 140 exits the external opening 210. The string 140 may then be tied to secure the string 140 to the insert member 130. As used herein, "tying" the string may include any suitable method of securing the inserted end of the string 140 to a portion of the string after inserting the end through the annular cavity 200 so that the string 140 is secured to the insert member 130. FIG. 8 shows a top view of the device 100 illustrating the insert member 130 and portions of two external openings 210.

The string 140 may be of a sufficient length to extend through the vaginal cavity 710 and outside of the patient's body when the medical device 100 is inserted in the cervical canal 730, as seen in FIG. 14. By pulling the string 140, the medical device 100 may be removed through the vaginal cavity 710 without forceps or a similar device. Alternatively, the string 140 may be permanently attached to the insert member 130. For instance, the device 100 may be molded such that one end of the string 140 is molded into the insert member 130.

Figure 3:
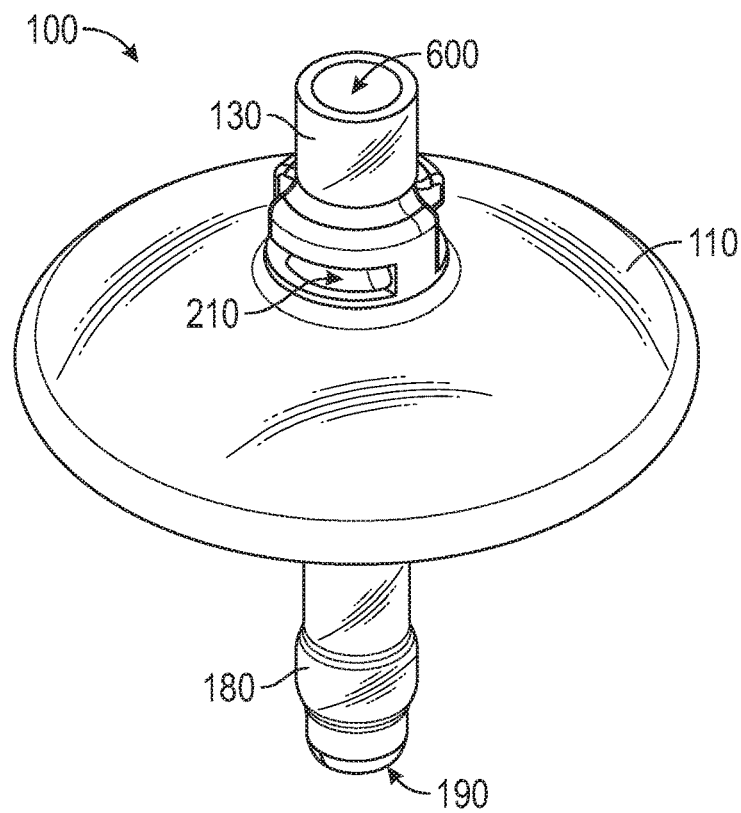
FIG. 3 shows a perspective view of a device in accordance with the present disclosure.
Figure 12:
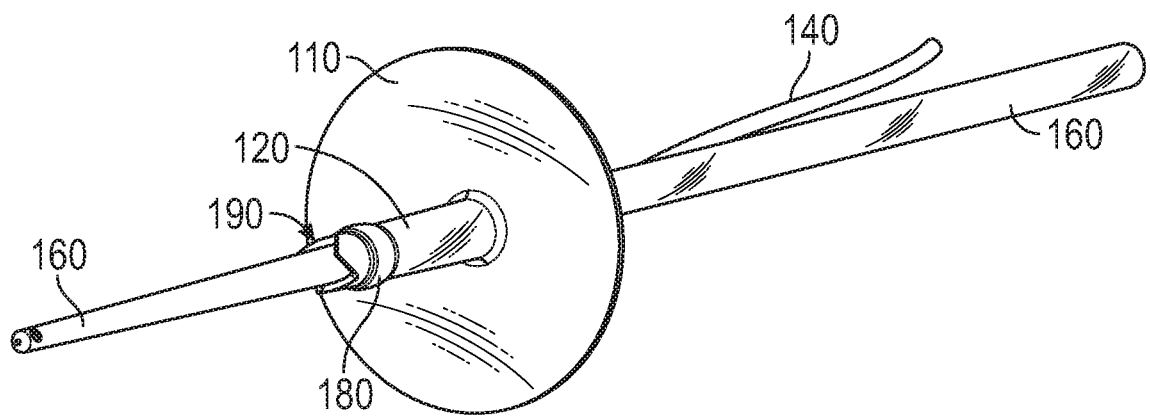
FIG. 12 shows a perspective view of a device with a catheter inserted through the device in accordance with the present disclosure.

As shown in FIG. 7, the medical device 100 may have a bore 150 extending longitudinally through the arm 120 and through the shield 110 such that the bore 150 has an opening 610 at the distal end 122 of the arm 120 and an opening 600 on the side of the shield 110 opposite the arm 120. The bore 150 may extend through the insert member 130 such that the opening 600 on the side of the shield 110 opposite the arm 120 is located at the end of the insert member 130, as shown in FIG. 3. Thus, the bore 150 may extend completely through the device 100 in a generally straight line. When the device 100 is in place during use, as shown in FIG. 14, the bore 150 creates a passageway between the vaginal cavity 710 and the cervical canal 730 or uterine cavity 740 through the device 100. To use the device 100, a catheter 160 may be inserted into the opening 600 of the bore 150 on the side of the shield 110 opposite the arm 120 and pushed through the bore 150 and then through the opening 610 at the distal end 122 of the arm 120, as shown in FIGS. 12-14. The bore 150 is of sufficient diameter to allow the catheter 160 to pass therethrough. Accordingly, the medical device 100 may function as a guide or cannula to facilitate passage for the catheter 160, which may be used as an insemination catheter for introducing a semen sample into a patient's reproductive system. In this manner, the medical device 100 may be utilized during intracervical or intrauterine insemination procedures for introducing a semen sample into the cervical canal 730 or the uterine cavity 740, as desired. The catheter 160 may then be removed while leaving the device 100 in place.

Figure 2:
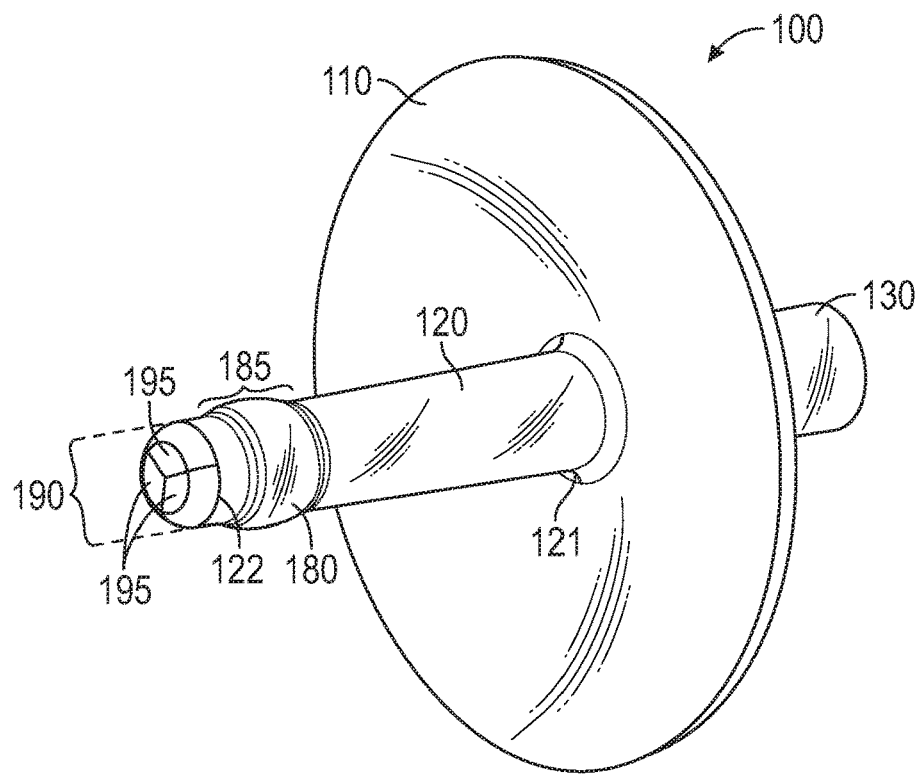
FIG. 2 shows a perspective view of a device in accordance with the present disclosure.
Figure 9:
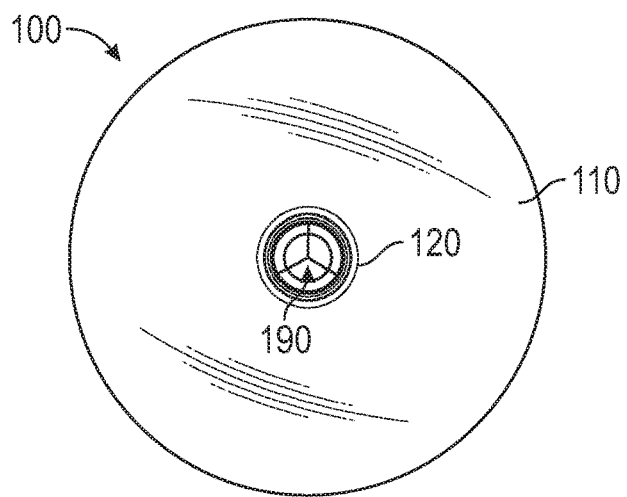
FIG. 9 shows a bottom plan view of a device in accordance with the present disclosure.
Figure 11:
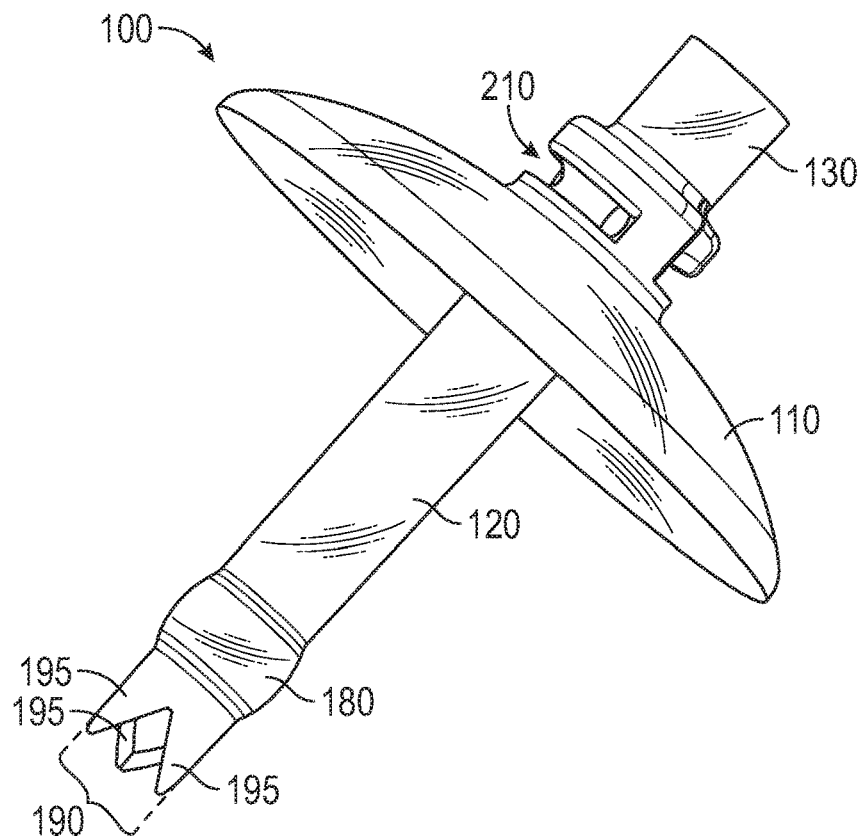
FIG. 11 shows a perspective view of a device in accordance with the present disclosure.

The device 100 may further comprise a valve 190 disposed at the distal end 122 of the arm 120. The valve 190 is operable between an open position, as shown in FIGS. 10 and 11, and a closed position, as shown in FIGS. 1 and 2. The valve 190 comprises a plurality of elastomeric flaps 195 integrally attached to the distal end 122 of the arm 120. The elastomeric flaps 195 are resiliently biased inwardly toward the center of the bore 150 and against each other when the valve 190 is in the closed position. The elastomeric flaps 195 are sized and shaped to form a substantially fluid-tight seal over the opening 610 at the distal end 122 of the arm 120 when the valve 190 is in the closed position. As used herein, the term "elastomeric" refers to any material that is flexible and/or stretchable such that the material can flex and/or stretch and then return to its original position. In this case, the original position refers to the closed position of the valve. Preferably, the valve 190 has three elastomeric flaps 195 each having a generally triangular shape, as best seen in FIG. 2. The three triangular flaps 195 fit together when the valve 190 is in the closed position to form a substantially fluid-tight seal to prevent fluid leakage through the valve 190. FIG. 9 shows a bottom view of the device 100 with the valve 190 in the closed position.

During an artificial insemination procedure, an insemination catheter 160 may pass through the entirety of the device 100. When the catheter 160 is pushed through the opening 610 at the distal end 122 of the arm 120, as shown in FIGS. 12 and 13, the catheter 160 forces the elastomeric flaps 195 of the valve 190 outward, as best seen in FIGS. 11 and 12, thereby moving the valve 190 into the open position. In this manner, a catheter 160 may pass through the medical device 100, deliver a semen sample to a patient's cervical canal 730 or uterine cavity 740, and then be removed from the medical device while leaving the device 100 in place. Upon delivery of the semen sample, the insemination catheter 160 may be entirely or partially removed from the medical device 100. When the catheter 160 is removed, the elastomeric flaps 195 of the valve 190 move to their original position, thereby moving the valve 190 to the closed position. When the valve 190 is in the closed position, the semen sample is prevented from exiting the cervical canal 730 via the bore 150 and thus cannot leak back through the medical device 100 into the vaginal cavity 710. Thus, the medical device 100 may effectively function both as a cannula for an insemination instrument and as a cervical plug that prevents semen that has been introduced into the patient's cervical canal 730 or uterine cavity 740 from leaking into the patient's vaginal cavity 710.

The present disclosure may also be directed to a method for artificial insemination. The medical device 100 may be configured to function as a cervical plug, as shown in FIG. 14. A semen sample may first be introduced into a patient's cervical canal 730 or uterine cavity 740, depending on whether intracervical insemination or intrauterine insemination is utilized. The semen sample may be introduced artificially into the patient's reproductive system or, alternatively, the sample may be introduced into a patient's reproductive system during sexual intercourse. After the semen sample is introduced into the cervical canal 730 or uterine cavity 740, the medical device 100 may be inserted into the cervical canal 730 of the patient such that the arm 120 extends into the patient's cervical canal 730 and the shield 110 substantially covers the external os 720 of the patient's cervix, as shown in FIG. 14. As previously noted, FIG. 14 illustrates the device 100 being used with a syringe 170 and catheter 160, though the device 100 may be used as a cervical plug without the syringe 170 and catheter 160 by inserting the device 100 into the position shown in FIG. 14 and leaving the device in place. If used only as a cervical plug, the bore 150 extending through the device 100 and the valve 190 disposed at the distal end 122 of the arm 120 may be optional features. Once the device 100 is secured in place with the arm 120 inserted into the cervical canal 730 and the shield 110 covering the external os 720, the shield 110 and the arm 120 of the medical device 100 prevent the semen sample from leaking from the cervical canal 730 into the patient's vaginal cavity 710. The circumferential bulge 180 of the arm 120 provides resistance to removal of the arm 120 of the device 100 from the cervical canal 730, thereby helping to ensure that the device 100 stays in place during use, as shown in FIG. 14. In this manner, the medical device 100 may increase the efficacy of intracervical or intrauterine insemination by reducing semen sample loss. After a suitable period of time, the device 100 may be removed.

It is understood that the medical device 100 used within the contemplated method, wherein the medical device 100 is configured to function as a cervical plug, may have some or all of the structural features consistent with the embodiments detailed above. Moreover, it is understood that the method of the present disclosure contemplates methodologies requiring additional or fewer steps dependent upon the presence of such structural features. For instance, the method may further comprise the step of removing the medical device 100 via the insert member 130 using forceps or a similar instrument. Alternatively, the device may be removed by pulling the device 100 through the vaginal cavity 710 via the string 140.

The medical device 100 may be configured to additionally function as a guide or cannula for a catheter, as shown in FIGS. 12-14. The medical device 100 has a bore 150 extending therethrough, a valve 190 disposed at the distal end 122 of the arm 120, and an optional circumferential bulge 180 positioned along a length 185 of the arm 120. The device 100 may be inserted into the cervical canal 730 of the patient such that the arm 120 extends into the patient's cervical canal 730 and the shield 110 substantially covers the external os 720 of the patient's cervix. A catheter 160 may be inserted into the bore 150 through the opening 600 on the side of the shield 110 opposite the arm 120. When inserting the catheter 160 into the bore 150, the catheter 160 may be pushed through the opening 610 at the distal end 122 of the arm 120, thereby forcing the valve 190 into the open position, as shown in FIG. 12, as far as desired for a particular insemination procedure. A semen sample may then be introduced into the patient's cervical canal 730 or uterine cavity 740 via the catheter 160.

The catheter 160 may be partially inserted into the bore 150 prior to inserting the device 100 into the cervical canal 730, and the catheter 160 may then be pushed through the opening 610 and the valve 190 at the distal end 122 of the arm 120 after inserting the medical device 100. Alternatively, the catheter 160 may be inserted into the bore 150 and through the valve 190 after inserting the medical device 100, or the catheter 160 may be inserted into the bore 150 such that the catheter 160 is pushed through the opening 610 and the valve 190 at the distal end 122 of the arm 120 prior to insertion of the device 100, as shown in FIGS. 12 and 13.

The elastomeric flaps 195 of the valve 190 are resiliently biased against each other when the valve 190 is in the closed position, as shown in FIG. 2. As the catheter 160 is inserted into the bore 150, the catheter 160 may be pushed through the opening 610 at the distal end 122 of the arm 120 so that the catheter 160 forces the elastomeric flaps 195 outward, thereby moving the valve 190 to the open position. The catheter 160 may be partially inserted into the bore 150 prior to inserting the device 100 into the cervical canal 730 such that the valve 190 remains in a closed position. The catheter 160 may then be pushed through the opening 610 at the distal end 122 of the arm 120 such that the valve 190 moves to the open position after insertion of the medical device 100 into the cervical canal 730.

Once the device 100 is secured in place with the arm 120 inserted into the cervical canal 730, the shield 110 covering the external os 720, and the catheter 160 inserted into the bore 150 and through the valve 190, a semen sample may be introduced into a patient's cervical canal 730 or uterine cavity 740, depending on whether intracervical insemination or intrauterine insemination is utilized, via the catheter 160. The sample may be introduced into the cervical canal 730 or uterine cavity 740 by injecting the semen sample through the catheter 160 using a syringe 170, as shown in FIG. 14. After introduction of the semen sample, the catheter 160 may be removed while leaving the device 100 in place. After removal of the catheter 160, the resiliently biased elastomeric flaps 195 of the valve 190 return to their original position, as shown in FIG. 2, in which the valve 190 is in a closed position, thereby preventing the semen sample from flowing back through the valve 190 and the bore 150. With the medical device 100 secured in place, the shield 110 and the arm 120 of the device 100 prevent the semen sample from leaking from the cervical canal 730 around the device 100 and into the patient's vaginal cavity 710, thereby increasing the efficacy of intracervical or intrauterine insemination by reducing semen sample loss. The circumferential bulge 180 of the arm 120 helps to keep the device 100 secured in place to prevent leakage around the device 100.

After a suitable period of time, the device 100 may be removed. The device 100 may be removed via the insert member 130 using forceps or a similar instrument. Alternatively, the device may be removed by pulling the device 100 through the vaginal cavity 710 via the string 140.

To ensure the semen sample is introduced into the proper location, the catheter 160 may extend entirely through the medical device 100 such that one end of the catheter 160 is located in the cervical canal 730 or in the uterine cavity 740 before directing the semen sample through the catheter 160. FIG. 14 illustrates a catheter 160 extending through the entirety of the device 100 into the uterine cavity 740 of a patient and a syringe 170 for injecting the sample. Alternatively, the semen sample may be directed through the bore 150 of the medical device 100 using a syringe 170 or similar instrument without the aid of a catheter 160.

The overall size or specific dimensions of components of the present device 100 may be varied to accommodate different patients. As one example, the device 100 may have the following dimensions: The shield 110 may be circular with a diameter of 22.50 mm; the arm 120 may be cylindrical with a diameter of 3.40 mm; and the circumferential bulge 180 may have a diameter of 4.46 mm at its widest point and extend along a length 185 of the arm 120 of 3.18 mm. These dimensions are illustrative only and are not intended to be limiting.

The present disclosure may also be directed to an insemination kit, which may be used by a health care provider or by a patient at home. The insemination kit may comprise: a medical device 100 having the features described herein, wherein the medical device 100 functions both as a cervical plug and a guide or cannula for a catheter; a catheter 160; and a syringe 170 configured to secure to the catheter 160. The catheter 160 and the syringe 170 of the kit may optionally be permanently attached to each other or molded together as a single component.

The insemination kit may be supplied to a user with the components pre-assembled such that the catheter 160 is inserted into the bore 150 of the medical device 100, and the syringe 170 is secured to one end of the catheter 160. The catheter 160 may be partially inserted into the bore 150 of the medical device 100 such that the valve 190 is in a closed position upon user receipt. Alternatively, the catheter 160 may be inserted into the bore 150 of the medical device 100 such that the catheter 160 extends through the opening 610 in the distal end 122 of the arm 120 so that the valve 190 is in an open position upon user receipt.

It is understood that versions of the invention may come in different forms and embodiments. Additionally, it is understood that one of skill in the art would appreciate these various forms and embodiments as falling within the scope of the invention as disclosed herein.

What is claimed is:

1. A medical device comprising:
a shield configured to cover an orifice;
an arm having a proximal end secured to the shield and a distal end configured to insert into an orifice, wherein the shield and the arm are configured to secure the medical device in place during use,
wherein the medical device has a bore extending longitudinally through the arm and through the shield such that the bore has an opening at the distal end of the arm and an opening on the side of the shield opposite the arm; and
a valve disposed at the distal end of the arm, wherein the valve is operable between an open position and a closed position, wherein the valve comprises a plurality of elastomeric flaps integrally attached to the distal end of the arm, wherein the elastomeric flaps are resiliently biased against each other when the valve is in the closed position, wherein the elastomeric flaps are each sized and shaped to form a substantially fluid-tight seal over the opening at the distal end of the arm when the valve is in the closed position.

2. The medical device of claim 1, wherein the valve has three elastomeric flaps.

3. The medical device of claim 1, wherein the arm has a circumferential bulge positioned along a length of the arm between a midway point of the arm and the distal end of the arm.

4. The medical device of claim 1, wherein the bore is of sufficient diameter to allow a catheter to pass through the bore.

5. The medical device of claim 1, wherein the shield has a concave shape, wherein the proximal end of the arm is secured to the concave side of the shield.

6. The medical device of claim 1, further comprising an insert member secured to the shield, wherein the insert member is secured to the opposite side of the shield as the proximal end of the arm.

7. The medical device of claim 6, wherein the insert member has an annular cavity, and wherein the insert member has an external opening that provides external access to the annular cavity.

8. The medical device of claim 1, wherein the shield is flexible.

9. The medical device of claim 1, wherein the shield is translucent.

* * * * *